US012502210B2

(12) United States Patent
Wall

(10) Patent No.: US 12,502,210 B2
(45) Date of Patent: Dec. 23, 2025

(54) SURGICAL INSTRUMENT AND METHOD

(71) Applicant: WARSAW ORTHOPEDIC INC., Warsaw, IN (US)

(72) Inventor: Daniel Paxton Wall, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 195 days.

(21) Appl. No.: 18/461,288

(22) Filed: Sep. 5, 2023

(65) Prior Publication Data

US 2024/0122630 A1 Apr. 18, 2024

Related U.S. Application Data

(63) Continuation of application No. 17/527,491, filed on Nov. 16, 2021, now Pat. No. 11,779,376.

(51) Int. Cl.
*A61B 17/88* (2006.01)
*A61B 17/70* (2006.01)

(52) U.S. Cl.
CPC ................................ *A61B 17/7082* (2013.01)

(58) Field of Classification Search
CPC .................................................. A61B 17/7082
USPC .......................................... 606/90, 104, 86 A
See application file for complete search history.

(56) References Cited

U.S. PATENT DOCUMENTS

| | | | | |
|---|---|---|---|---|
| 8,172,847 B2 * | 5/2012 | Dziedzic | A61B 17/7091 606/86 A |
| 8,777,954 B2 * | 7/2014 | McLean | A61B 17/7085 606/86 A |
| 10,448,978 B2 | 10/2019 | Wall et al. | |
| 11,779,376 B2 * | 10/2023 | Wall | A61B 17/7091 606/86 A |
| 2013/0282019 A1 * | 10/2013 | Bouliane | A61B 17/888 606/104 |
| 2014/0114363 A1 * | 4/2014 | Stevenson | A61B 17/7082 606/305 |
| 2015/0282855 A1 * | 10/2015 | Bess | A61B 17/8875 606/86 A |
| 2017/0135735 A1 * | 5/2017 | Hawkes | A61B 17/7076 |
| 2018/0303522 A1 | 10/2018 | Wall et al. | |
| 2019/0029736 A1 * | 1/2019 | Wall | A61B 17/7091 |
| 2020/0121397 A1 * | 4/2020 | Elliott | A61B 17/7074 |
| 2020/0121398 A1 * | 4/2020 | Elliott | A61B 90/39 |
| 2020/0297393 A1 * | 9/2020 | Olea | A61B 17/7086 |
| 2020/0337744 A1 * | 10/2020 | Grizzard | A61B 17/864 |
| 2021/0000519 A1 * | 1/2021 | Erramilli | A61B 17/8863 |

* cited by examiner

*Primary Examiner* — Eduardo C Robert
*Assistant Examiner* — David C Comstock
(74) *Attorney, Agent, or Firm* — Sorell, Lenna & Schmidt, LLP

(57) ABSTRACT

A surgical instrument includes a first member and an actuator disposed with the first member. An assembly is provided that includes a second member engageable with a bone fastener receiver. A third member is rotatable relative to the second member and threadably engageable with the bone fastener receiver to capture the bone fastener receiver. Systems, spinal constructs, implants and methods are disclosed.

20 Claims, 9 Drawing Sheets

SURGICAL INSTRUMENT AND METHOD

CROSS REFERENCE TO RELATED APPLICATIONS

This application is a continuation of U.S. patent application Ser. No. 17/527,491, filed Nov. 16, 2021, which is expressly incorporated by reference herein, in its entirety.

TECHNICAL FIELD

The present disclosure generally relates to medical devices for the treatment of musculoskeletal disorders, and more particularly to a surgical system and method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal implants such as vertebral rods and/or fasteners are often used to provide stability to a treated region. Rods redirect stresses away from a damaged or defective region while healing takes place to restore proper alignment and generally support vertebral members. During surgical treatment, spinal implants can be delivered to a surgical site, for example, so that the rods may be attached via the fasteners to the exterior of two or more vertebral members. Surgical treatment may employ surgical instruments and implants that are manipulated for engagement with vertebrae to position and align one or more vertebrae. This disclosure describes an improvement over these prior technologies.

SUMMARY

In one embodiment, a surgical instrument is provided. The surgical instrument includes a first member and an actuator disposed with the first member. An assembly includes a second member engageable with a bone fastener receiver and a third member that is rotatable relative to the second member and threadably engageable with the bone fastener receiver to capture the bone fastener receiver. In some embodiments, systems, spinal constructs, implants and methods are disclosed.

In some embodiments, the surgical instrument includes a driver and an actuator disposed with the driver. An assembly includes an outer sleeve engageable with a bone fastener receiver and an inner sleeve being rotatable with the actuator. The inner sleeve is rotatable relative to the outer sleeve and threadably engageable with the bone fastener receiver to capture the bone fastener receiver.

In some embodiments, the surgical instrument includes a driver including a shaft and a flange. The driver includes an actuator disposed adjacent to the flange and is rotatable relative to the shaft. An assembly includes an outer sleeve engageable with a bone fastener receiver and an inner sleeve having a collar being releasably connectable with the actuator such that the inner sleeve is rotatably fixed with the actuator. The inner sleeve is rotatable relative to the outer sleeve and threadably engageable with the bone fastener receiver to capture the bone fastener receiver.

BRIEF DESCRIPTION OF THE DRAWINGS

The present disclosure will become more readily apparent from the specific description accompanied by the following drawings, in which.

DETAILED DESCRIPTION

Figure 1:
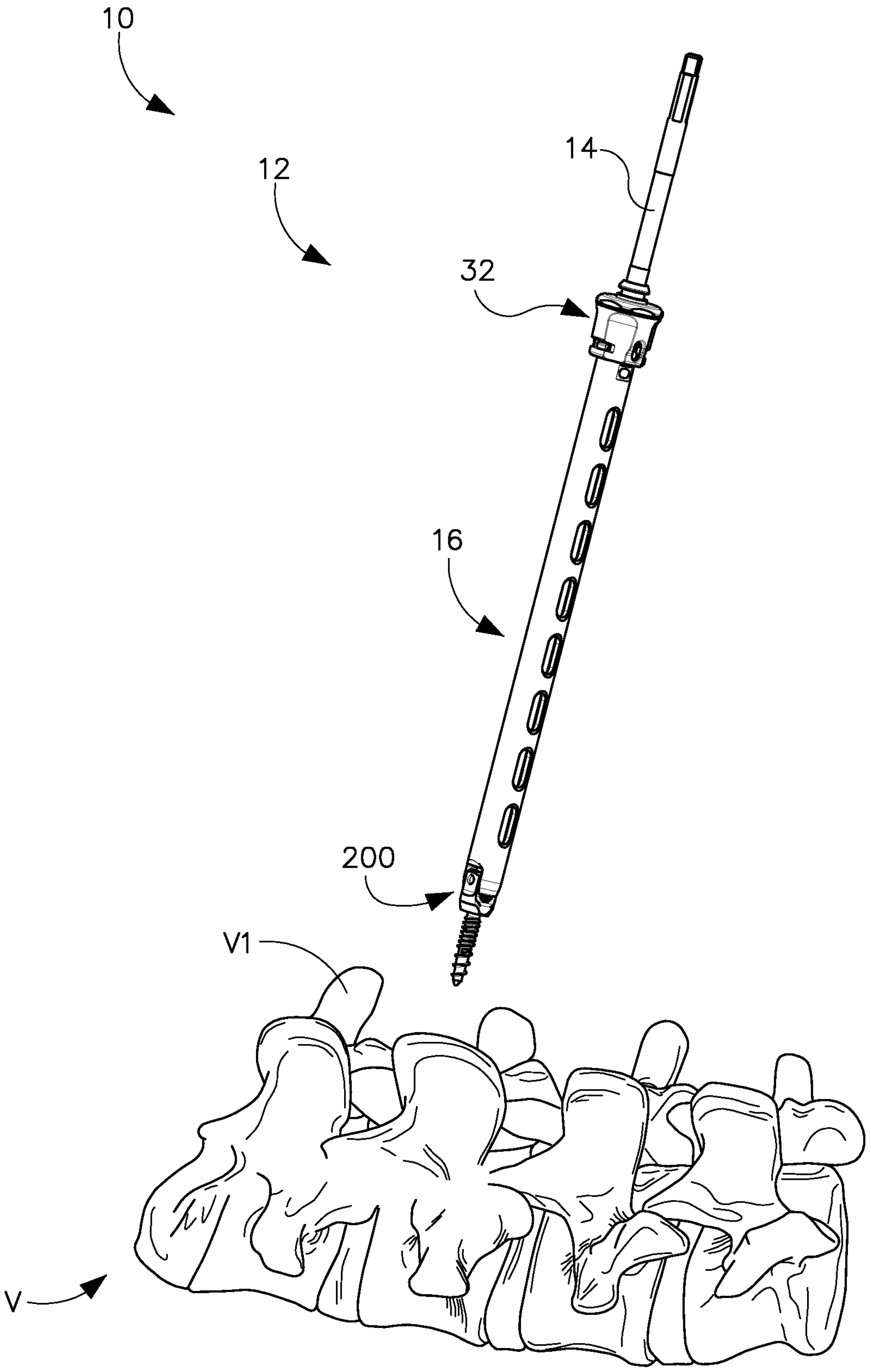
FIG. 1 is a perspective view of components of one embodiment of a surgical system in accordance with the principles of the present disclosure disposed with vertebrae.

The exemplary embodiments of the surgical system and related methods of use disclosed are discussed in terms of medical devices for the treatment of musculoskeletal disorders and more particularly, in terms of a spinal implant system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system includes a surgical instrument, for example, a driver configured for use with surgical navigation. In some embodiments, the driver includes an assembly including an inner sleeve and an outer sleeve that is configured for releasable connection with an actuator for engagement and capture of a receiver of a bone fastener. In some embodiments, the receiver is connected with a shank of the bone fastener. In some embodiments, the assembly is configured to releasably connect and disconnect from the driver such that the driver can capture alternatively configured bone fasteners via alternatively configured assemblies and/or sleeves. In some embodiments, the driver includes a shank sleeve. In some embodiments, the driver is configured to releasably connect and disconnect with the shank sleeve such that the shank sleeve can be replaced with the assembly. In some embodiments, the assembly can be assembled during manufacture, prior to surgery and/or during surgery.

In some embodiments, the bone fastener includes a bone screw. In some embodiments, the bone screw includes a receiver attached to a shank of the bone screw. In some embodiments, the receiver is pre-assembled with the shank prior to a surgical procedure. In some embodiments, the receiver can be assembled with the shank before, during or after the surgical procedure. In some embodiments, the bone screw is delivered through an arm guide of a robot. In some embodiments, the arm guide includes a diameter of 13.48 or 15.6 mm.

In some embodiments, the present surgical system includes a driver configured for engagement with an assembly including an inner sleeve and an outer sleeve. In some embodiments, the outer sleeve is configured for attachment to a receiver of a bone screw. In some embodiments, the outer sleeve is configured for disposal with a portion of the driver and engagement with a knob. In some embodiments, the inner sleeve is configured for threaded engagement with the receiver. In some embodiments, the inner sleeve is configured for engagement with the knob.

In some embodiments, the present surgical system includes an assembly including an inner sleeve and an outer sleeve. In some embodiments, the outer sleeve is configured for connection and engagement with the inner sleeve. In some embodiments, the outer sleeve is configured to translate relative to the inner sleeve. In some embodiments, the inner sleeve is configured to rotate about a key on a driver shaft.

In some embodiments, the present surgical system includes a driver that is configured for fixation with a head of a bone screw. In some embodiments, the driver includes an actuator including a knob that is translationally fixed to a shaft of the driver and is configured to rotate about a portion of the fixed shaft. In some embodiments, the actuator includes a collar that is engageable with an assembly. In some embodiments, the collar is configured to rotate and translate relative to the knob. In some embodiments, the assembly includes an inner sleeve and an outer sleeve. In some embodiments, the outer sleeve is configured for axial translation relative to the driver and the inner sleeve is configured for rotational engagement relative to the driver.

In some embodiments, the present surgical system described above includes a method of loading a bone screw with a surgical driver, the method including the steps of engaging a receiver of the bone screw with a distal end of the driver. In some embodiments, the method includes the step of positioning and engaging a head of the bone screw with an end of the driver. In some embodiments, the end of the driver includes a tip configuration. In some embodiments, the end of the driver includes a star shaped tip configuration (see, for example, a similar star shaped tip configuration of Torx® (Acument Global Technologies, Inc., Sterling Heights, Michigan, USA)). In some embodiments, the method includes the step of translating an outer sleeve of the driver in a direction, for example, a distal direction, and surfaces, for example, flats of the outer sleeve engage surfaces, for example, flats of the receiver. In some embodiments, the method includes the step of manually retaining/holding the outer sleeve and the receiver while a knob of the driver is rotated such that an inner sleeve disposed with the outer sleeve is rotated to threadingly engage with inner threaded surface of the receiver. In some embodiments, the method includes the step of finally tightening the bone screw with the driver. In some embodiments, tightening of the bone screw with the driver includes retaining/holding the outer sleeve while rotating the knob.

In some embodiments, the present surgical system includes a surgical instrument that can be employed with an end effector of a robotic arm to facilitate implantation with the robotic arm. In some embodiments, the surgical instrument is guided through the end effector for a guide-wireless screw insertion. In some embodiments, the surgical instrument comprises a robotic guided screw driver employed with robotic and/or navigation guidance, which may include an image guide.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-12, there are illustrated components of a spinal implant system 10, in accordance with the principles of the present disclosure.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a fully open surgical procedure, a minimally invasive procedure including percutaneous techniques, and mini-open surgical techniques to deliver and introduce instrumentation and/or a spinal implant, such as, for example, a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 5:
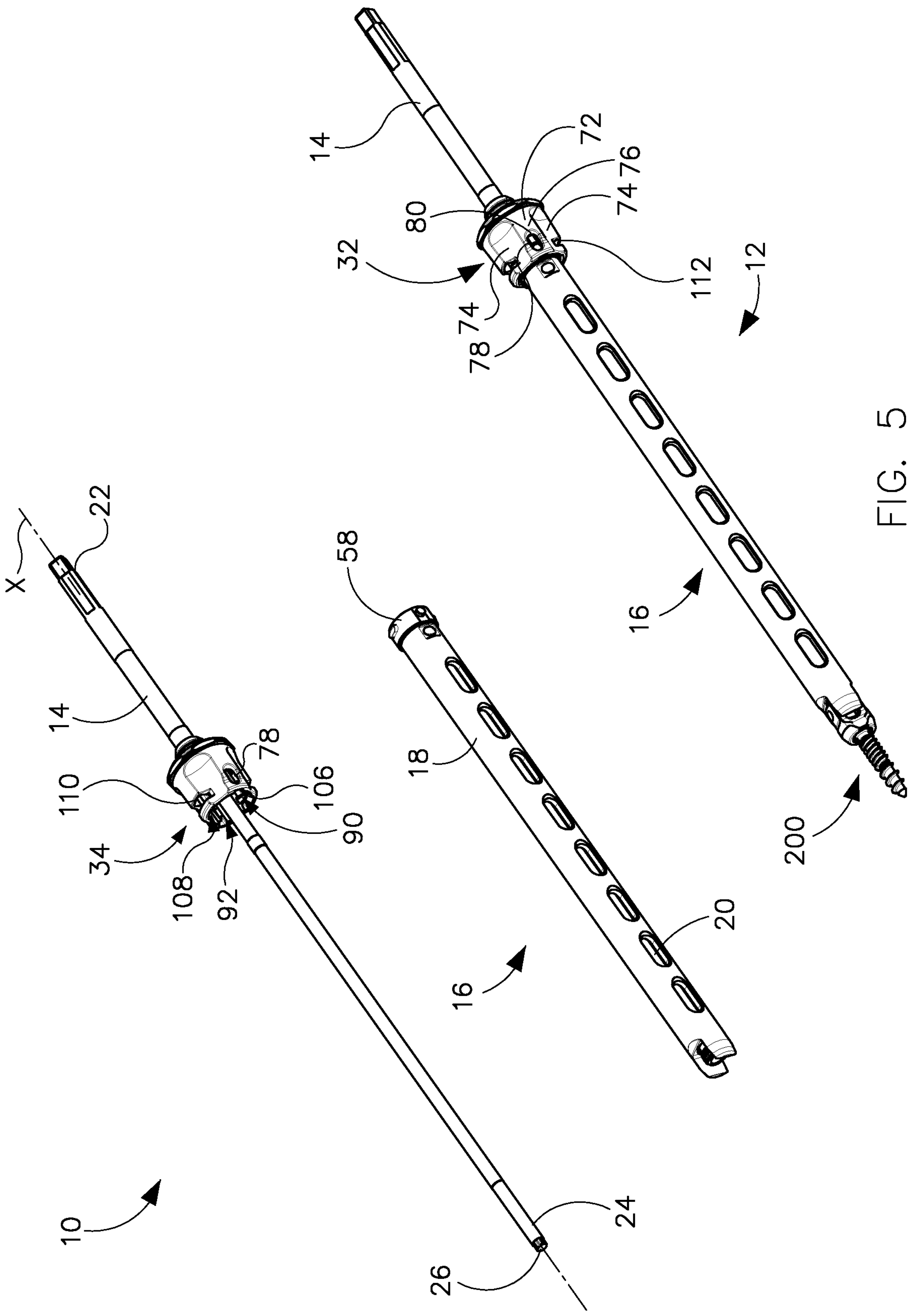
FIG. 5 is a perspective view of components of the surgical system shown in FIG. 1 with parts separated.
Figure 9:
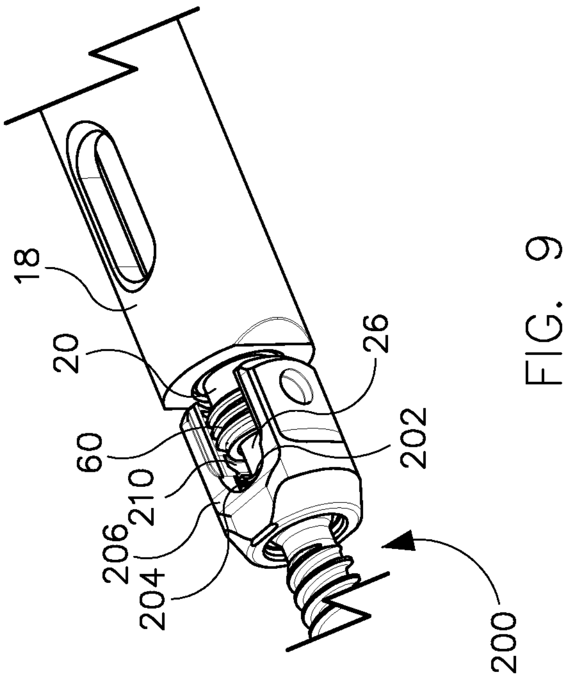
FIG. 9 is a break away view of components of the surgical system shown in FIG. 1.
Figure 12:
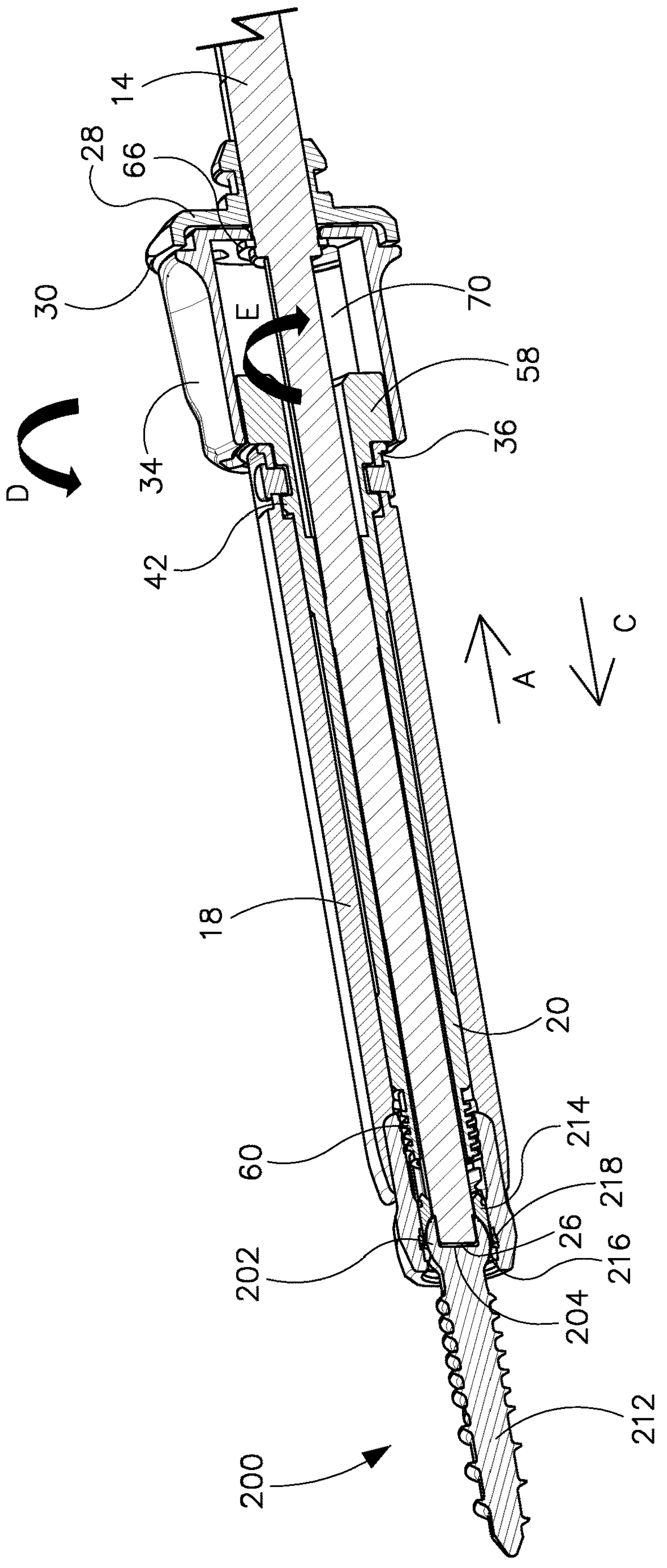
FIG. 12 is a cross section view of components of the surgical system shown in FIG. 1.

Spinal implant system 10 includes a surgical instrument 12. Surgical instrument 12 is configured for connection with an implant, for example, a bone fastener 200, as shown in FIG. 1. Surgical instrument 12 includes a member, for example, a driver 14. Driver 14 is configured for engagement with a member, for example, an inner sleeve 20 of an assembly 16, as described herein. Driver 14 extends between an end 22 and an end 24 and defines a longitudinal axis X disposed therebetween, as shown FIG. 5. End 22 is configured for engagement with a component, for example, a navigation component (not shown), as described herein. End 24 includes a drive 26, as shown in FIG. 5, which is connectable with a head 202 including a drive socket 204 of bone fastener 200, as shown in FIGS. 9 and 12. Drive 26 includes a shaped tip configuration. In some embodiments, drive 26 may have different cross-section configurations, including square, hexagonal, polygonal, triangular, star or hexalobe. In some embodiments, end 24 may have alternate surface configurations, including, smooth, rough, arcuate, undulating, porous, semi-porous, dimpled, polished and/or textured.

Figure 6:
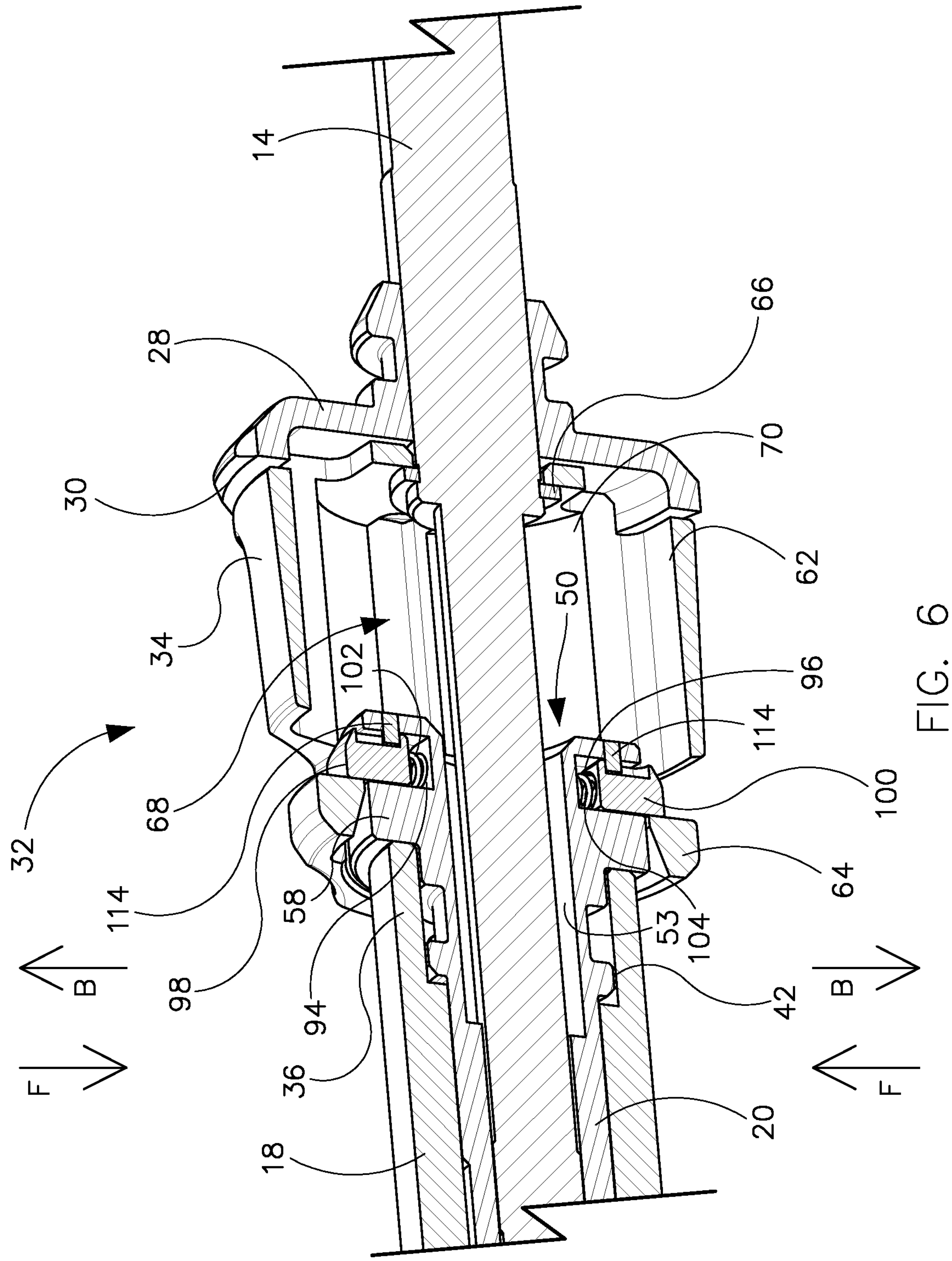
FIG. 6 is a break away cross section view of components of the surgical system shown in FIG. 1.

Driver 14 includes a bushing 28, as shown in FIG. 6. Bushing 28 is configured for connection with the navigation component. In some embodiments, bushing 28 can be alternatively connected with the navigation component, for example, monolithic, integral connection, frictional engagement, threaded engagement, mutual grooves, screws, adhesive, nails, barbs and/or raised element. See, for example, similar surgical navigation components and their use as described in U.S. Pat. Nos. 6,021,343, 6,725,080, 6,796,988, the entire contents of each of these references being incorporated by reference herein.

Bushing 28 is connected to a surface of driver 14. In some embodiments, bushing 28 is press fit welded to a surface of driver 14. Bushing 28 includes a flange 30 configured for engagement with a component of an actuator 32, for example, a knob 34, as shown in FIG. 6, and described herein. Flange 30 is configured to contact a surface of knob 34 and is configured to engage knob 34 to translationally fix knob 34 with driver 14. In some embodiments, flange 30 is configured to prevent loosening of knob 34 during use.

Figure 2:
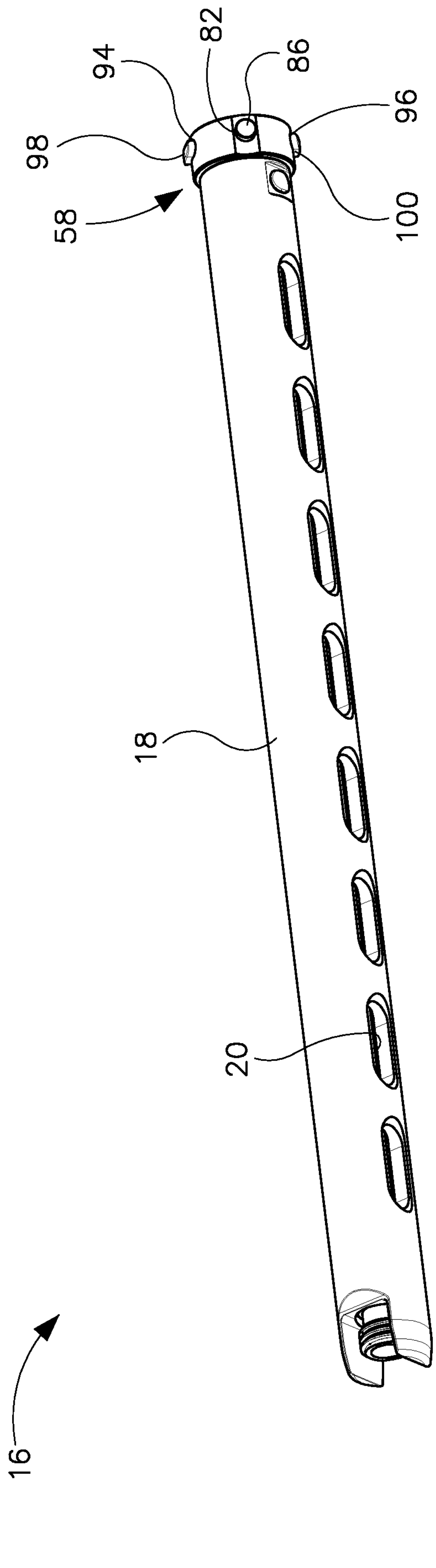
FIG. 2 is a perspective view of components of the surgical system shown in FIG. 1.
Figure 3:
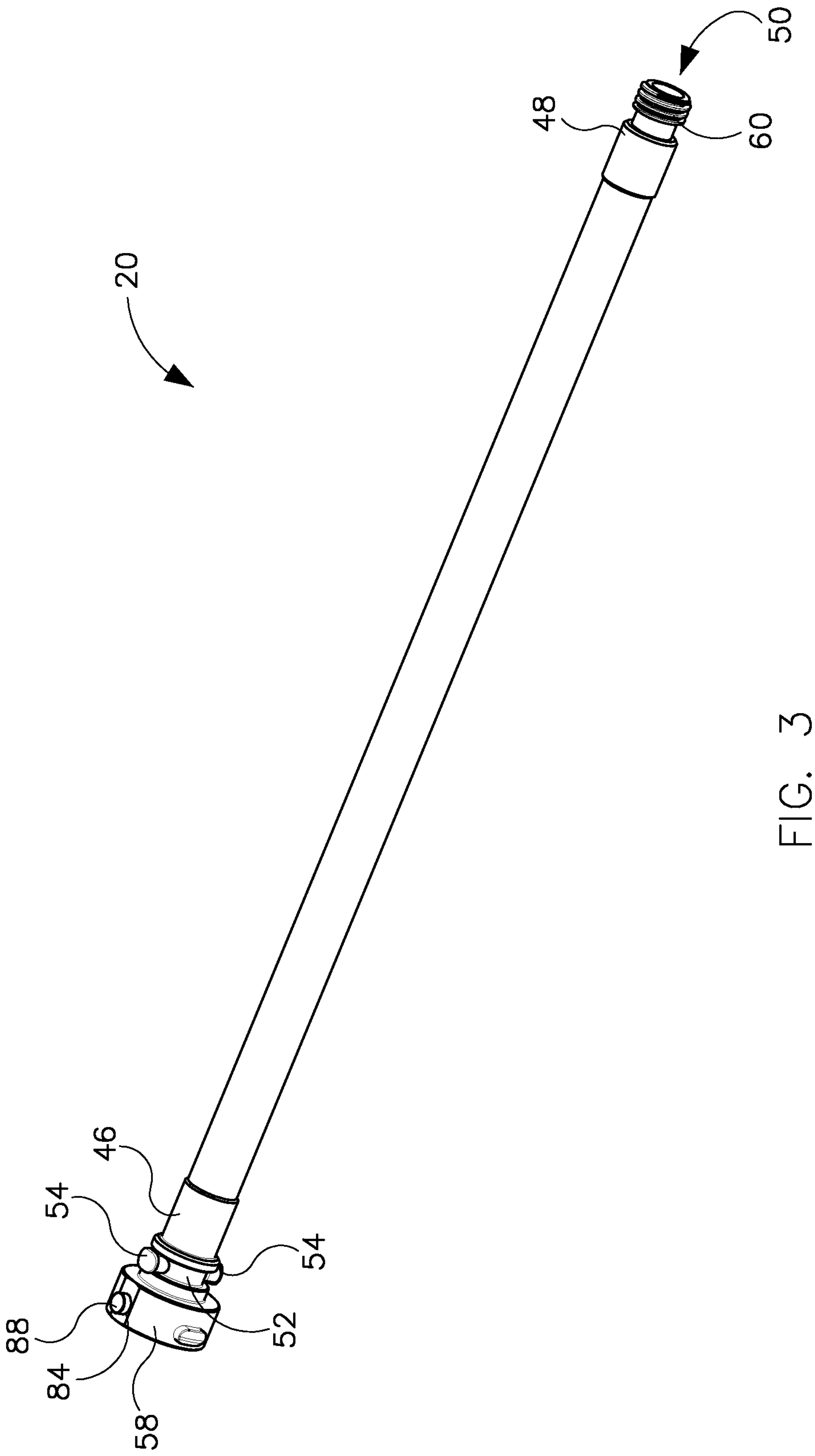
FIG. 3 is a perspective view of components of the surgical system shown in FIG. 1.
Figure 4:
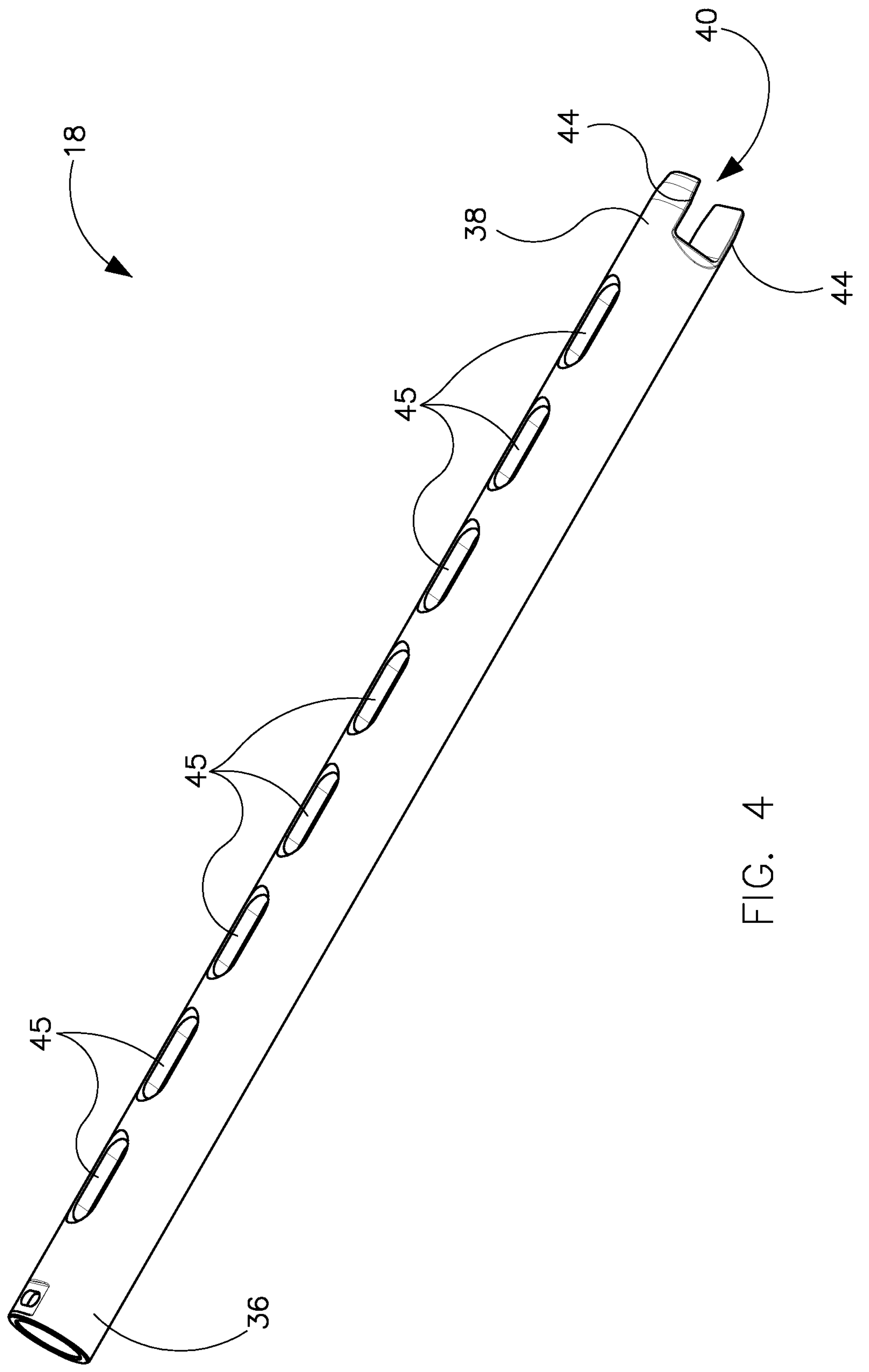
FIG. 4 is a perspective view of components of the surgical system shown in FIG. 1.

Assembly 16 includes inner sleeve 20 and a member, for example, an outer sleeve 18, as shown in FIGS. 2-4. Assembly 16 is configured for connection with actuator 32 for engagement and capture of bone fastener 200. In some embodiments, assembly 16 is configured for releasable connection with alternately configured drivers. Outer sleeve 18 is configured for axial translation within knob 34 and engagement with a receiver 206 of bone fastener 200. Outer sleeve 18 is tubular, extending between an end 36 and an end 38. In some embodiments, outer sleeve 18 may have alternate cross section configurations, for example, oval, oblong, triangular, square, polygonal, irregular, uniform, non-uniform, offset, staggered, undulating, arcuate, variable and/or tapered. In some embodiments, outer sleeve 18 may have alternate surface configurations, for example, smooth, rough, arcuate, undulating, porous, semi-porous, dimpled, polished and/or textured.

Outer sleeve 18 includes an inner surface that defines a passageway 40 that is coaxial with longitudinal axis X and is configured for disposal of inner sleeve 20, as described herein. In some embodiments, passageway 40 may have alternate surface configurations, for example, smooth, rough, arcuate, undulating, porous, semi-porous, dimpled, polished and/or textured.

Figure 8:
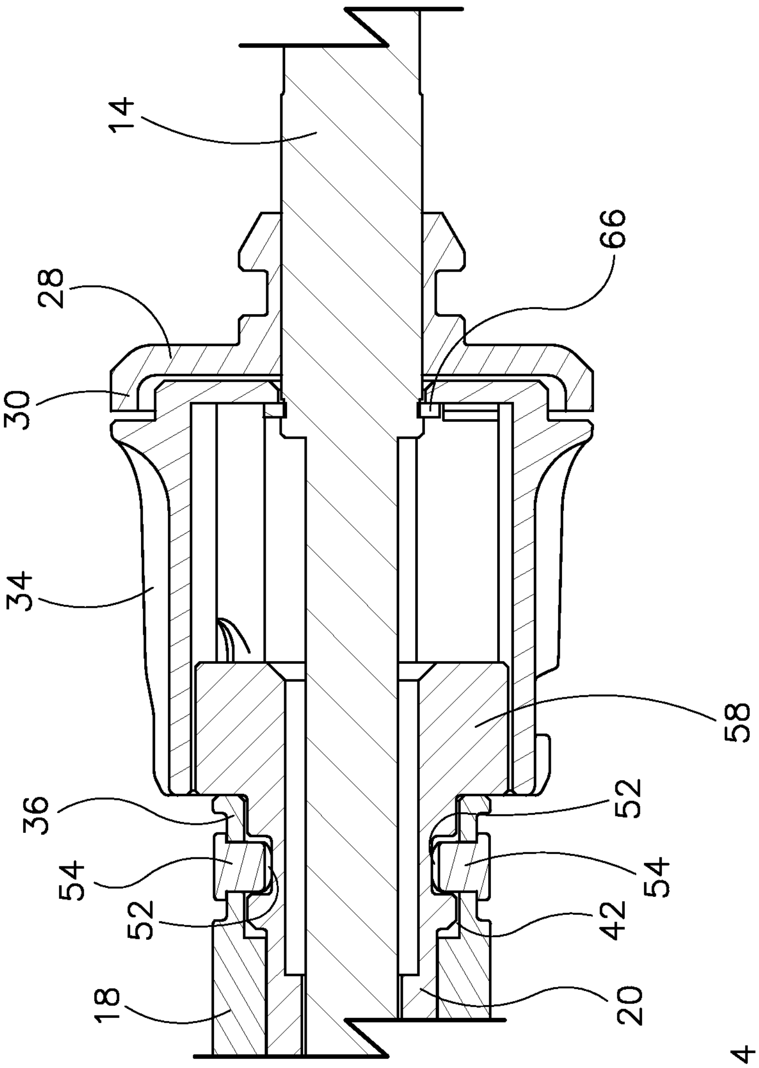
FIG. 8 is a break away cross section view of components of the surgical system shown in FIG. 1.

End 36 includes an inner surface that defines a ledge 42, as shown in FIGS. 6 and 8. Ledge 42 is configured for engagement with a circumferential groove 52 of inner sleeve 20, as described herein. Ledge 42 translationally fixes inner sleeve 20 relative to outer sleeve 18, as described herein. In some embodiments, ledge 42 may have alternate surface configurations, for example, smooth, rough, arcuate, undulating, porous, semi-porous, dimpled, polished and/or textured.

Figure 10:
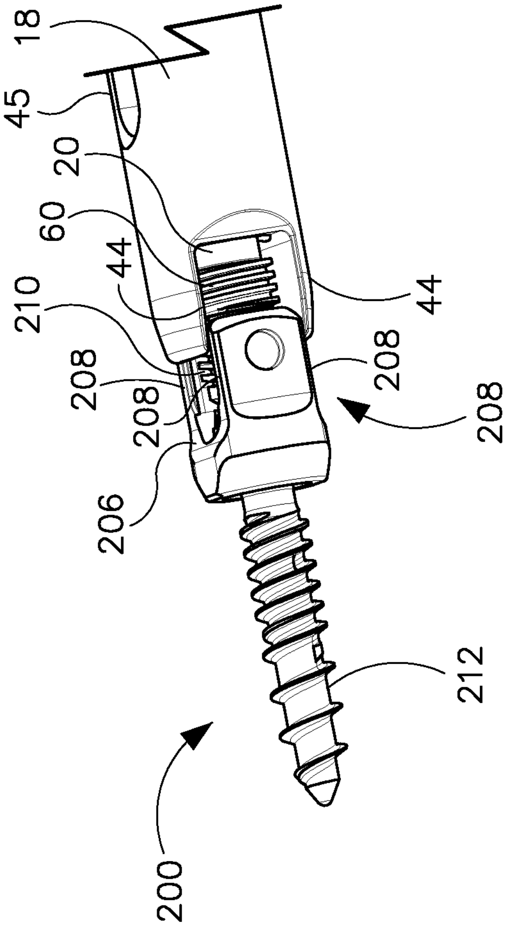
FIG. 10 is a break away view of components of the surgical system shown in FIG. 1.
Figure 11:
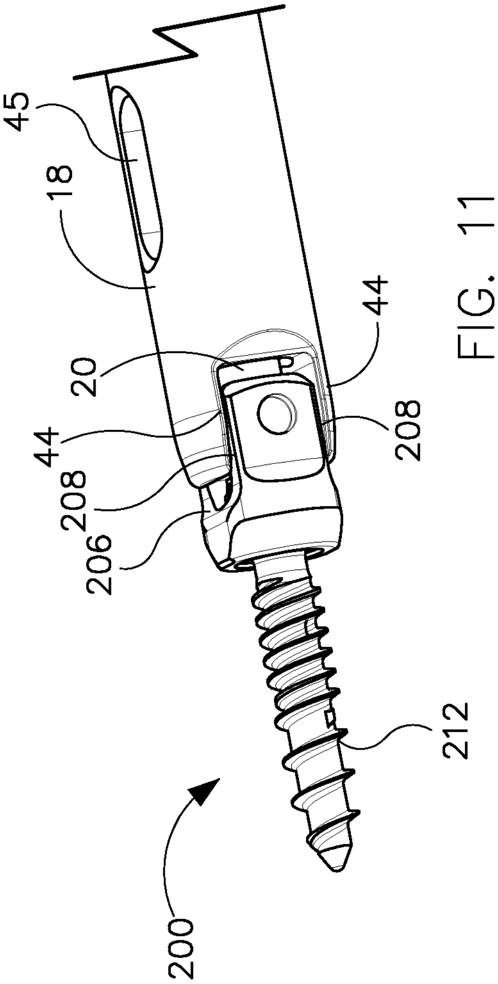
FIG. 11 is a break away view of components of the surgical system shown in FIG. 1.

End 38 includes mating surfaces, for example, flats 44 that are configured for engagement with mating surfaces, for example, flats 208 of receiver 206, as shown in FIGS. 4, 10 and 11. In some embodiments, flats 44, 208 may have alternately shaped configurations, for example, oval, oblong, triangular, square, polygonal, irregular, uniform, non-uniform, offset, staggered, undulating, arcuate, variable and/or tapered.

Outer sleeve 18 includes an outer surface that defines windows 45, as shown in FIG. 4. Windows 45 are configured to facilitate cleaning of surgical instrument 12. In some embodiments, windows 45 may have alternate cross section configurations, for example, oval, oblong, triangular, square, polygonal, irregular, uniform, non-uniform, offset, staggered, undulating, arcuate, variable and/or tapered.

Inner sleeve 20 is tubular, extending between an end 46 and an end 48, as shown in FIG. 3. Inner sleeve 20 is configured for disposal with outer sleeve 18 and is threadably engageable with receiver 206 to capture receiver 206, as described herein. Inner sleeve 20 is rotatable relative to outer sleeve 18. In some embodiments, inner sleeve 20 may have alternate cross section configurations, for example, oval, oblong, triangular, square, polygonal, irregular, uniform, non-uniform, offset, staggered, undulating, arcuate, variable and/or tapered. In some embodiments, inner sleeve 20 may have alternate surface configurations, for example, smooth, rough, arcuate, undulating, porous, semi-porous, dimpled, polished and/or textured.

Figure 7:
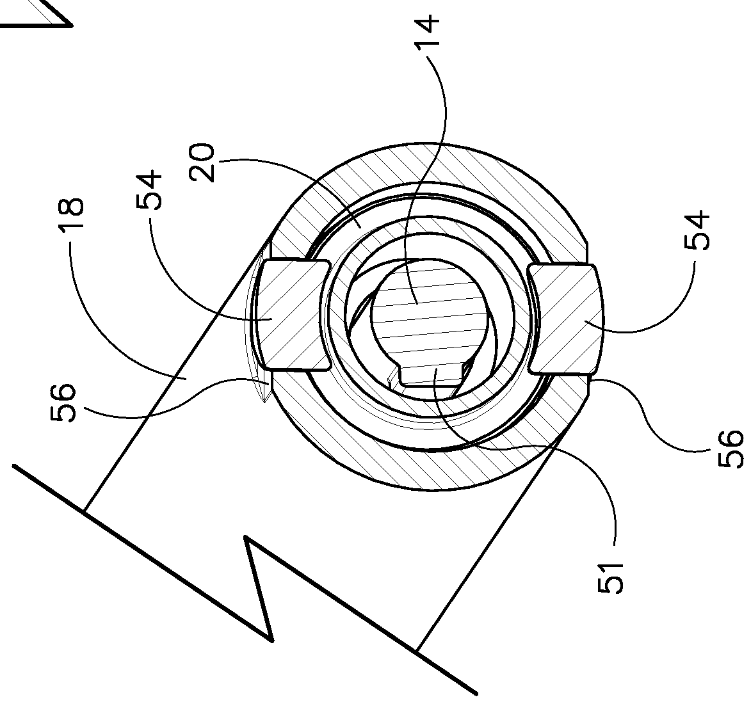
FIG. 7 is a break away cross section view of components of the surgical system shown in FIG. 1.

Inner sleeve 20 includes an inner surface that defines a passageway 50, as shown in FIGS. 3 and 6. Passageway 50 is coaxial with longitudinal axis X and is configured for disposal of driver 14, as described herein. Inner sleeve 20 is configured for rotation about driver 14. Inner sleeve 20 rotates about driver 14 and a counterbore 53 of inner sleeve 20 prevents engagement of inner sleeve 20 with a key 51 of driver 14 such that key 51 is rotationally and axially cleared, as shown in FIGS. 6 and 7. In some embodiments, passageway 50 may have alternate surface configurations, for example, smooth, rough, arcuate, undulating, porous, semi-porous, dimpled, polished and/or textured.

End 46 includes circumferential groove 52 and buttons 54 configured for rotational engagement with ledge 42, as shown in FIGS. 7 and 8. Buttons 54 are configured for engagement with openings 56 at end 36 of outer sleeve 18. In some embodiments, circumferential groove 52 may have alternative surface configurations, for example, smooth, rough, arcuate, undulating, porous, semi-porous, dimpled, polished and/or textured. End 46 is configured for connection with a component of actuator 32, for example, an adjustment collar 58, as described herein. End 46 is monolithic and rotationally fixed with adjustment collar 58. In some embodiments, end 46 is not monolithic with adjustment collar 58.

End 48 includes a threaded portion 60, as shown in FIGS. 3, 9 and 10. Threaded portion 60 is configured for engagement with a threaded inner surface 210 of receiver 206 to capture bone fastener 200, as shown in FIGS. 9 and 10. Inner sleeve 20 is rotated relative to outer sleeve 18 to capture bone fastener 200, as described herein. In some embodiments, threaded portion 60 may have alternative surface configurations, for example, smooth, rough, arcuate, undulating, porous, semi-porous, dimpled, polished and/or textured. In some embodiments, selected portions or all of threaded portion 60 may have alternate cross-section configurations, for example, oval, oblong, triangular, rectangular, square, polygonal, irregular, uniform, non-uniform, variable, tubular and/or tapered.

Actuator 32 includes knob 34 and adjustment collar 58. See, for example, the embodiments and disclosure of systems and methods of components of an actuator, shown and described in commonly owned and assigned U.S. patent application Ser. No. 17/527,485 filed Nov. 16, 2021, and published as U.S. Patent Application Publication No. 2023/0149055, on May 18, 2023, the entire contents of which being incorporated herein by reference.

Knob 34 extends between an end 62 and an end 64, as shown in FIG. 6. A retaining ring 66 is configured for disposal at end 62. Retaining ring 66 is configured for engagement with a portion of driver 14 and an inner surface of bushing 28, as shown in FIG. 6, such that knob 34 is translationally fixed with retaining ring 66 and flange 30 but is configured to rotate relative to driver 14. Knob 34 is releasably connectable with assembly 16 via adjustment collar 58, and outer sleeve 18 is translatable relative to knob 34 via adjustment collar 58, as described herein. Knob 34 defines a cavity 68. An interior wall 70 of knob 34 is configured for slidable engagement with an outer surface of adjustment collar 58, as shown in FIG. 6. In some embodiments, cavity 68 may have alternate cross section configurations, for example, oval, oblong, triangular, square, polygonal, irregular, uniform, non-uniform, offset, staggered, undulating, arcuate, variable and/or tapered.

Knob 34 defines an exterior gripping surface 72 that includes at least one indent 74, as shown in FIG. 5. In some embodiments, gripping surface 72 may have alternative surface configurations, for example, smooth, rough, arcuate, undulating, porous, semi-porous, dimpled, polished and/or textured.

Knob 34 includes a wall 76 that defines a pair of opposing windows 78, as shown in FIG. 5. Windows 78 are configured to display indicia, for example, pins 86, 88 of adjustment collar 58 to indicate translation/positioning of outer sleeve 18 relative to knob 34, as described herein. Wall 76 includes inner surfaces 80, as shown in FIG. 5. Inner surfaces 80 are tapered. In some embodiments, inner surfaces 80 are tapered to increase visibility of pins 86, 88. In some embodiments, windows 78 may have alternate cross section configurations, for example, oval, oblong, triangular, square, polygonal, irregular, uniform, non-uniform, offset, staggered, undulating, arcuate, variable and/or tapered.

Adjustment collar 58 is configured to releasably connect assembly 16 with knob 34, translate outer sleeve 18 with knob 34 and rotate inner sleeve 20 relative to outer sleeve 18, as described herein. Adjustment collar 58 includes a surface that defines a recess 82 and a recess 84, as shown in FIGS. 2 and 3. Recess 82 is disposed opposite of recess 84. Pin 86 is configured for fixed engagement with recess 82 and pin 88 is configured for fixed engagement with recess 84. Pin 86 is configured for slidable engagement with an interior slot 90 of wall 70 of knob 34 and pin 88 is configured for slidable engagement with an interior slot 92 of wall 70 of knob 34 for translation of adjustment collar 58 within knob 34, as shown in FIG. 5. Pins 86, 88 are translated within slots 90, 92 respectively and during selected translation of outer sleeve 18, pins 86, 88 are viewable via windows 78 of knob 34, as shown in FIG. 5. In some embodiments, pins 86, 88 are laser welded to recesses 82, 84. In some embodiments, all or a portion of pins 86, 88 are laser marked a selected color, for example, black. In some embodiments, pins 86, 88 are manufactured in one or more selected colors, for example, pink, red, orange, yellow, green, blue, purple, brown, white and/or black. In some embodiments, pins 86, 88 are anodized and/or PVD coated.

Adjustment collar 58 includes a surface that defines a recess 94 and a recess 96, as shown in FIGS. 2 and 6. Recess 94 is disposed opposite of recess 96. A button 98 is configured for disposal with recess 94 and a button 100 is configured for disposal with recess 96, as shown in FIG. 6. Buttons 98, 100 are configured to facilitate disengagement of assembly 16 with knob 34. Button 98 is biased, for example, via a pair of springs 102 and button 100 is biased, for example, via a pair of springs 104, as shown in FIG. 6. In some embodiments, springs 102 and 104 include a force of 1 to 4 lbs when contracted. Button 98 is configured for slidable engagement with an interior slot 106 of wall 70 of knob 34 and button 100 is configured for slidable engagement with an interior slot 108 of wall 70 of knob 34, as shown in FIG. 5. Buttons 98, 100 are translated within slots 106, 108 respectively to dispose buttons 98, 100 with transverse openings 110, 112 respectively of knob 34, as shown in FIG. 5. Buttons 98, 100 are configured for snap engagement with openings 110, 112. Pins 114 are configured to retain buttons 98, 100 with adjustment collar 58, as shown in FIG. 6. In some embodiments, buttons 98, 100 include plungers.

Bone fastener 200 includes head 202 including drive socket 204 configured for engagement with driver 14, and receiver 206 configured for engagement with end 38 of outer sleeve 18 and end 48 of inner sleeve 20. Bone fastener 200 includes an elongated shaft 212 configured for penetrating tissue, as shown in FIGS. 10-12. Bone fastener 200 includes a crown 214 and includes expandable elements 216, 218 configured for disposal within an interior of receiver 206, as shown in FIG. 12. In some embodiments, selected portions or all of bone fastener 200 may have alternate cross-section configurations, for example, oval, oblong, triangular, rectangular, square, polygonal, irregular, uniform, non-uniform, variable, tubular and/or tapered. In some embodiments, selected portions or all of bone fastener 200 may have alternate surface configurations, for example, smooth and/or surface configurations to enhance engagement with tissue, for example, rough, arcuate, undulating, porous, semi-porous, dimpled, polished and/or textured.

Shaft 212 has a cylindrical cross section configuration and includes an outer surface having an external thread form. In some embodiments, the thread form may include a single thread turn or a plurality of discrete threads. In some embodiments, other engaging structures may be disposed on shaft 212, for example, a nail configuration, barbs, expanding elements, raised elements and/or spikes to facilitate engagement of shaft 212 with tissue, for example, vertebrae.

In some embodiments, the outer surface of shaft 212 may include one or a plurality of openings. In some embodiments, all or only a portion of shaft 212 may be disposed at alternate orientations, relative to a longitudinal axis of bone fastener 200, for example, transverse, perpendicular and/or other angular orientations such as acute or obtuse, co-axial and/or may be offset or staggered. In some embodiments, all or only a portion of shaft 212 may be cannulated.

In assembly, operation and use, spinal implant system 10, similar to the systems and methods described herein, is employed with a surgical procedure, for example, a treatment of an applicable condition or injury of an affected section of a spinal column and adjacent areas within a body. In some embodiments, one or all of the components of spinal implant system 10 can be delivered or utilized as a pre-assembled device or can be assembled in situ. Spinal implant system 10 may be completely or partially revised, removed or replaced.

In some embodiments, spinal implant system 10 is employed with an end effector (not shown) of a robotic arm (not shown) to facilitate implantation with the robotic arm. In some embodiments, spinal implant system 10 is employed with robotic and/or navigation guidance (including a navigation component (not shown)), which may include an image guide.

Surgical instrument 12 is assembled prior to the surgical procedure. In some embodiments, assembly 16 is configured to releasably connect and disconnect from driver 14 such that driver 14 can capture alternatively configured bone fasteners via alternatively configured assemblies and/or sleeves. In some embodiments, driver 14 includes a shank sleeve (not shown) that is configured for connection to a bone fastener (not shown) including a shank. See, for example, the embodiments and disclosure of systems and methods of components of a shank sleeve, shown and described in commonly owned and assigned U.S. patent application Ser. No. 17/527,485 filed Nov. 16, 2021, and published as U.S. Patent Application Publication No. 2023/0149055, on May 18, 2023, the entire contents of which being incorporated herein by reference. In some embodiments, driver 14 is configured to releasably connect and disconnect with the shank sleeve such that the shank sleeve can be replaced with assembly 16 to capture receiver 206 of bone fastener 200. In some embodiments, assembly 16 can be assembled during manufacture, prior to surgery and/or during surgery.

To releasably connect assembly 16 with knob 34, adjustment collar 58 attached to inner sleeve 20 and in engagement with outer sleeve 18, is translated in a direction shown by arrow A in FIG. 12. Adjustment collar 58 engages wall 70 of knob 34, as shown in FIG. 12. Pins 86, 88 slidably engage slots 90, 92 and buttons 98, 100 are depressed and engage with slots 106, 108. Buttons 98, 100 are disposed with openings 110, 112 as springs 102, 104 expand to translate buttons 98, 100 in an upward direction, as shown by arrows B in FIG. 6, in a snap fit engagement of buttons 98, 100 with openings 110, 112 thereby releasably connecting assembly 16 with knob 34.

To connect surgical instrument 12 with bone fastener 200, driver 14 via drive 26 engages with drive socket 204 of bone fastener 200. Driver 14 is held rigid by a user and outer sleeve 18 is manually translated in a direction, for example, a distal direction, as shown by arrow C in FIG. 12 until threaded portion 60 of inner sleeve 20 contacts threaded inner surface 210 of receiver 206. Knob 34 is rotated in a direction, as shown by arrow D in FIG. 12 to rotate inner sleeve 20 via adjustment collar 58 to engage threaded portion 60 with threaded inner surface 210 as flats 44 of outer sleeve 18 matingly engage flats 208 of receiver 206 to capture bone fastener 200, as shown in FIGS. 11 and 12. Driver 14 via drive 26 engages socket 204 to drive and fix bone fastener 200 with tissue, for example, a vertebra V1 of vertebrae V, shown in FIG. 1.

To disconnect bone fastener 200 from surgical instrument 12, knob 34 is rotated in a direction, shown by arrow E in FIG. 12. Inner sleeve 20 rotates as outer sleeve 18 is translated in a direction, for example, a proximal direction, as shown by arrow A. As outer sleeve 18 is translated, driver 14 disengages from socket 204 of bone fastener 200 respectively.

In some embodiments, spinal implant system 10 includes an agent, which may be disposed, packed, coated or layered within, on or about the components and/or surfaces of spinal implant system 10. In some embodiments, the agent may include bone growth promoting material, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

Upon completion of the procedure, the surgical instruments, assemblies and non-implanted components of spinal implant system 10 are removed from the surgical site and the incision is closed.

To disassemble/disconnect assembly 16 from knob 34, buttons 98, 100 are simultaneously translated in a downward direction, as shown by arrows F in FIG. 6. Buttons 98, 100 are translated into slots 106, 108 as assembly 16 outer is disconnected from knob 34 and translated in a direction, as shown by arrow C in FIG. 12. In some embodiments, an instrument or pusher (not shown) is provided to translate buttons 98, 100 in the downward direction to facilitate disconnection of assembly 16 from knob 34.

One or more of the components of spinal implant system 10 can be made of radiolucent materials such as polymers. Radiomarkers may be included for identification under x-ray, fluoroscopy, CT or other imaging techniques. In some embodiments, surgical instrument 12 is guided to the surgical site via a guidewire, for example, a K-wire (not shown) and/or without the use of an image guide, as described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:

a driver including an end connectable with a bone fastener drive socket;

an actuator disposed with the driver; and an assembly including an outer sleeve having mating surfaces engageable with a bone fastener receiver, and an inner sleeve being rotatable relative to the outer sleeve, the inner sleeve having a collar being releasably connectable with the actuator such that the inner sleeve is rotatably fixed with the actuator, the inner sleeve being threadably engageable with the bone fastener receiver to capture the bone fastener receiver, wherein the actuator includes a wall having at least one slot and at least one window, and the collar having at least one pin engageable with the at least one slot and aligned with the at least one window.

2. A surgical instrument as recited in claim 1, wherein the at least one slot includes a first slot and a second slot, and the at least one pin includes a first pin and a second pin.

3. A surgical instrument as recited in claim 1, wherein the wall includes at least one opening and the collar includes at least one button disposable with the at least one opening via a snap engagement.

4. A surgical instrument as recited in claim 3, wherein the at least one button includes a first button and a second button, the buttons including plungers.

5. A surgical instrument as recited in claim 1, wherein the inner sleeve is rotatable relative to the collar.

6. A surgical instrument as recited in claim 1, wherein the inner sleeve includes a proximal end configured for connection with the collar.

7. A surgical instrument as recited in claim 6, wherein the proximal end includes a circumferential groove and at least one button configured for engagement with a ledge of an end of the outer sleeve.

8. A surgical instrument as recited in claim 7, wherein the at least one button of the inner sleeve is configured for engagement with at least one opening disposed at the end of the outer sleeve.

9. A surgical instrument comprising:

a driver including an end connectable with a bone fastener, a shaft, a flange and an actuator, the actuator disposed adjacent to the flange and being rotatable relative to the shaft; and an assembly including an outer sleeve engageable with a receiver of the bone fastener, and an inner sleeve connected with a collar and being releasably connectable with the actuator via a snap engagement such that the inner sleeve is rotatably fixed with the actuator, the outer sleeve having a distal end including at least one mating surface engageable with at least one mating surface of the bone fastener receiver, the inner sleeve being rotatable relative to the outer sleeve and threadably engageable with the bone fastener receiver to capture the bone fastener receiver, wherein the actuator includes a wall having at least one slot and at least one window, and the collar having at least one pin engageable with the at least one slot and aligned with the at least one window.

10. A surgical instrument as recited in claim 9, wherein the outer sleeve is configured for translation relative to a knob of the actuator.

11. A surgical instrument as recited in claim 9, wherein the inner sleeve includes a distal threaded portion and a proximal end configured for connection with the collar.

12. A surgical instrument as recited in claim 9, wherein the at least one slot includes a first slot and a second slot, and the at least one pin includes a first pin and a second pin.

13. A surgical instrument as recited in claim 9, wherein the wall includes at least one opening and the collar includes at least one button disposable with the at least one opening to form the snap engagement.

14. A surgical instrument comprising:

a driver including an end connectable with a bone fastener drive socket;

an actuator disposed with the driver; and an assembly including an outer sleeve having mating surfaces engageable with a bone fastener receiver, and an inner sleeve being rotatable relative to the outer sleeve, the inner sleeve having a collar being releasably connectable with the actuator such that the inner sleeve is rotatably fixed with the actuator, the inner sleeve being threadably engageable with the bone fastener receiver to capture the bone fastener receiver, wherein the inner sleeve includes a proximal end configured for connection with the collar, and wherein the proximal end includes a circumferential groove and at least one button configured for engagement with a ledge of an end of the outer sleeve.

15. A surgical instrument as recited in claim 14, wherein the at least one button of the inner sleeve is configured for engagement with at least one opening disposed at the end of the outer sleeve.

16. A surgical instrument as recited in claim 14, wherein the actuator includes a wall having at least one slot and at least one window, and the collar having at least one pin engageable with the at least one slot and aligned with the at least one window.

17. A surgical instrument as recited in claim 16, wherein the at least one slot includes a first slot and a second slot, and the at least one pin includes a first pin and a second pin.

18. A surgical instrument as recited in claim 16, wherein the wall includes at least one opening and the collar includes at least one button disposable with the at least one opening via a snap engagement.

19. A surgical instrument as recited in claim 18, wherein the at least one button includes a first button and a second button, the buttons including plungers.

20. A surgical instrument as recited in claim 14, wherein the inner sleeve is rotatable relative to the collar.

* * * * *